United States Patent [19]
Vandenbroek et al.

[11] Patent Number: 5,496,280
[45] Date of Patent: Mar. 5, 1996

[54] TROCAR VALVE ASSEMBLY

[75] Inventors: Frans Vandenbroek; Vincent C. Tangherlini, both of Rancho Santa Margarita, Calif.

[73] Assignee: Applied Medical Resources Corporation, Laguna Hills, Calif.

[21] Appl. No.: 245,916

[22] Filed: May 19, 1994

Related U.S. Application Data

[63] Continuation-in-part of Ser. No. 907,706, Jul. 2, 1992, abandoned.

[51] Int. Cl.$^6$ .................................................. A61M 39/22
[52] U.S. Cl. ............................................. 604/167; 604/256
[58] Field of Search .................................. 604/167, 256, 604/283

[56]              References Cited

U.S. PATENT DOCUMENTS

| | | |
|---|---|---|
| 3,861,416 | 1/1975 | Waichterle . |
| 4,143,853 | 3/1979 | Abramson . |
| 4,177,814 | 12/1979 | Knepshield et al. . |
| 4,222,126 | 9/1980 | Boretos et al. . |
| 4,240,411 | 12/1980 | Hosono ................................... 604/167 |
| 4,364,127 | 12/1982 | Pierce et al. . |
| 4,375,864 | 3/1983 | Savage . |
| 4,424,833 | 1/1984 | Spector et al. . |
| 4,475,548 | 10/1984 | Muto . |
| 4,492,253 | 1/1985 | Raftis . |
| 4,535,819 | 8/1985 | Atkinson et al. . |
| 4,566,493 | 1/1986 | Edwards et al. . |
| 4,673,393 | 6/1987 | Suzuki et al. . |
| 4,765,588 | 8/1988 | Atkinson . |
| 4,798,584 | 1/1989 | Hillsted . |
| 4,809,679 | 3/1989 | Shimonaka et al. . |
| 4,857,062 | 8/1989 | Russell .................................... 604/256 |
| 4,960,412 | 10/1990 | Fink ........................................ 604/167 |
| 5,010,925 | 4/1991 | Atkinson et al. . |
| 5,122,123 | 6/1992 | Vaillancourt ............................ 604/283 |
| 5,125,915 | 6/1992 | Berry ....................................... 604/283 |
| 5,141,498 | 8/1992 | Christian . |
| 5,167,636 | 12/1992 | Clement .................................. 604/167 |
| 5,197,955 | 3/1993 | Stephens et al. ....................... 604/167 |
| 5,269,763 | 12/1993 | Boehmer et al. ...................... 604/167 |

*Primary Examiner*—Paul J. Hirsch
*Attorney, Agent, or Firm*—Richard L. Myers

[57]              ABSTRACT

A trocar having a working channel extending along an axis between a distal end and a proximal end includes a cannula at the distal end and a housing at the proximal end which define a working channel of the trocar. A valve disposed in the working channel separates the trocar into regions proximal of the valve and regions distal of the valve. The valve includes elastomeric means which form a first seal that is openably closable across the working channel. A wall of the valve extends radially outwardly of the elastomeric means and forms a second seal with the housing. The trocar also includes means for defining a passage extending from regions exterior of the trocar through the regions proximal of the valve and into the regions distal of the valve. Valve means disposed across this passage controls the administration of fluid through the passage and into the working channel of the cannula.

14 Claims, 7 Drawing Sheets

TROCAR VALVE ASSEMBLY

CROSS REFERENCE TO RELATED APPLICATIONS

This application is a continuation-in-part of International Application PCT/US93/04709 filed on 18/May/1993 which is a continuation-in-part of U.S. patent application Ser. No. 07/907,706 filed on Jul. 2, 1992, now abandoned.

BACKGROUND OF THE INVENTION

1. Field of the Invention

This invention relates generally to access devices and more specifically to seals and insufflation mechanisms applicable to such devices.

2. Discussion of the Prior Art

Access devices are commonly used in surgery to facilitate the introduction of various surgical instruments into vessels, conduits, cavities, and other interior regions of the body. These access devices include, for example, devices which facilitate the introduction of a needle into a vessel, and trocars which facilitate the introduction of laparoscopic instruments into the abdomen of the body.

Some of these access devices are introduced into regions which include a fluid under pressure. In the case of a needle access device, this fluid may be a liquid such as blood. In the case of a trocar, this fluid may be a gas such as an insufflation gas. In either case it is desirable to provide for the introduction of the surgical instrument into the cavity without permitting the escape of the pressurized fluid.

In the case of trocars, a cannula at the distal end of the trocar is typically connected to a seal housing at the proximal end of the trocar. Together the cannula and housing form a working channel through which various instruments can be inserted to access the cavity. Seal mechanisms are commonly disposed in the housing and include a septum valve which seals the working channel when an instrument is in place, and a zero closure valve which seals the working channel when the instrument is removed.

Maintenance of an insufflation pressure has been accomplished by various structures associated with the trocar. In one case, an insufflation inlet is provided directly into the cannula distally of the housing. A valve associated with this inlet can be opened and closed to control the insufflation pressure. These valves and inlets have been particularly troublesome when incorporated into reusable trocars, where the intricacy of these structures has made them difficult to clean and sterilize for repeated use.

SUMMARY OF THE INVENTION

The present invention overcomes these difficulties associated with the prior art by providing an insufflation inlet and valve which are associated with the housing rather than the cannula. With this concept the housing can be formed of disposable materials so that the cleaning of these intricate structures no longer presents a problem.

The zero closure valve in the housing separates the trocar into regions distal of the valve and regions proximal of the valve. The valve includes elastomeric means which is openable to receive the instrument but closeable to form a seal in the absence of the instrument. A valve wall supports the elastomeric means in the working channel and forms a seal with the housing. The insufflation inlet is provided through the wall of the housing to provide fluid communication with the regions proximal of the valve. A manifold positioned proximally of the valve not only facilitates a seal between the valve and the housing, but also acts to form a passage through the valve wall into the working channel of the cannula. In one embodiment, the manifold includes a fenestration of windows disposed along the passage.

In one aspect of the invention, a trocar having a working channel extends along an axis between a distal end and a proximal end. The trocar includes a cannula having a tubular configuration and a wall which defines a working channel at the distal end of the trocar. The housing is disposed in fixed relationship to the cannula and defines the working channel at the proximal end of the trocar. A valve disposed in the working channel separates the channel into regions proximal of the valve and regions distal of the valve. Elastomeric means included in the valve forms a first seal which is openably closable across the working channel. A wall also included in the valve extends radially outwardly of the elastomeric means toward the housing. Portions of the housing engage the valve wall and form with the valve wall a second seal which is disposed generally outwardly of the first seal. Also included in the trocar is means for defining an insufflation passage extending from regions exterior of the trocar through the regions proximal of the valve and into the regions distal of the valve. Valve means is disposed across this passage for controlling the administration of a fluid from the regions exterior of the trocar through the passage and into the working channel of the cannula. A housing inlet defines a first section of the passage while portions of the valve define a second section of the passage between the first seal and the second seal of the valve. The manifold defines a third section of the passage between the first section and the second section.

In another aspect of the invention a trocar has a working channel which extends along an axis between a proximal end and an distal end. A cannula having a first axis and a tubular configuration includes a wall which extends distally from a proximal end of the cannula to define the working channel at the distal end of the trocar. A housing having a second axis and a wall which extends proximally from a distal end of the housing defines the working channel at the proximal end of the trocar. At least one seal is disposed in the housing across the working channel and proximally of the distal end of the housing. One of the cannula and the housing is formed of a sterilizable metal material while the other of the cannula and the housing is formed of a disposable plastic material. Means is disposed at the proximal end of the cannula and the distal end of the housing for releasibly joining the cannula to the housing with the first axis aligned with the second axis to form the working channel of the trocar. This releasable joining means in one embodiment takes the form of a bayonet connector having tabs on one of the cannula and the housing which register with a recess in the other of the cannula and the housing. A ramp is provided in the other of the cannula and the housing to receive the tabs and to guide the tabs to the recess.

These and other features and advantages will be more apparent with a description of preferred embodiments and best mode of the invention, and reference to the associated drawings.

DESCRIPTION OF PREFERRED EMBODIMENTS AND BEST MODE OF THE INVENTION

Figure 1:
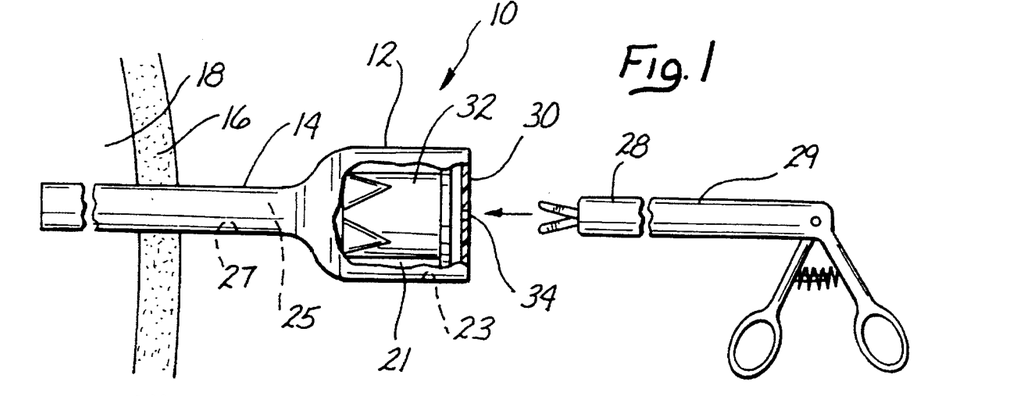
FIG. 1 is a side elevation view of a trocar partially cut away to illustrate a zero closure valve in one embodiment of the present invention.

A trocar is illustrated in FIG. 1 and designated generally by the reference numeral 10. The trocar 10 is represented of many types of surgical access devices which include a housing 12 and a cannula 14 which is adapted to extend across a body wall into a body cavity. In the case of the trocar 10, the cannula 14 is configured to extend through an abdominal wall 16 into a cavity, such as the abdominal cavity 18. The housing 12 includes a chamber 21 which is defined by an inner surface 23. This chamber 21 of the housing 12 communicates with a lumen 25 in the cannula 14 which is defined by an inner surface 27.

With these features, the trocar 10 is adapted to receive an instrument 28 having an elongate configuration and an outer surface 29. The instrument 28 is illustrated to be a pair of scissors having a length sufficient to pass through the trocar 10 and into the cavity 18 to perform a surgical operation.

Although scissors are illustrated in FIG. 1, it will be understood that the instrument 28 may include any variety of devices such as needles, retractors, scalpels, clamps and various other surgical devices.

The housing 12 is configured to provide structural support for a seal mechanism, which in the preferred embodiment includes an aperture or septum seal 30 and a zero closure seal 32. It is the function of these seals 30, 32 to prevent the escape of any pressurized fluid from the cavity 18 whether the instrument 28 is operatively disposed in the trocar 10 or whether the instrument 28 is removed from the trocar 10. In either case it is desirable that the valves 30, 32 be configured to produce minimal friction forces as the instrument 28 is inserted into and removed from the trocar 10.

with these conflicting requirements for an effective, low-friction seal, the valve 30 is typically provided with an aperture 34 which has a circular cross section. This shape for the aperture 34 enables it to closely engage the outer surface 29 of the instrument 28 and to form a seal round the instrument 28 when it is operatively disposed.

The valve 30 will typically be formed of an elastomeric material so that the aperture 34 is biased to seal against the outer surface 29. In order to avoid significant friction forces, this aperture 34 is preferably sized to a diameter slightly less than the diameter of the surface 29. However, since various instruments and various diameters for the outer surface 29 may be required in a particular surgery, the valve 30 will typically have a configuration wherein the size of the aperture 34 is expandable in order to accommodate a range of instrument sizes.

Particularly for instruments having larger diameters, the aperture 34 will have some minimum diameter greater than zero in a normal state. As a consequence, the valve 30 is open when the instrument 28 is not positioned in the trocar 10. Although it has been contemplated to provide septum valves 30 with apertures 34 which are closed in a normal state, these valves generate significant friction forces for instruments 28 having typically larger diameters. As a consequence, septum valves, such as the valve 30, are usually not relied upon to provide full closure when the instrument 28 is removed.

This purpose is more typically served by a valve, such as the valve 32, which is commonly referred to as a zero closure valve. As noted, such valves of the past have included flapper valves, which are complex and expensive, and duck-bill valves which are characterized by high friction forces.

A preferred embodiment of the zero closure valve 32 is illustrated in FIGS. 2–5. In this embodiment, the valve 32 has an axis 41 which extends from a distal end 43 to a proximal end 45. A cylindrical outer wall 50 has an outer surface 52, and an inner surface 54 best shown in FIG. 5. The outer wall 50 typically extends from the distal end 43 toward the proximal end 45 where it engages an enlarged flange 56. This flange 56 extends radially outwardly of the wall 52 and is configured to form a seal with the housing 12 of the trocar 10.

Of particular interest to the present invention is the distal end of the valve 32 which is configured to provide reduced friction forces when the instrument 28 is inserted, as well as zero closure characteristics when the instrument 28 is removed. This distal end 43 includes three or more fold sections such as those designated by the reference numerals 61a, 61b, 61c, and 61d in FIG. 2.

In the illustrated embodiment, each of these sections has components which are similar to those in other sections. For simplicity, the reference numerals associated with these components will be the same, followed by a letter which designates the associated folding section. When the similar components are referred to collectively, the letters will be omitted.

Figure 5:
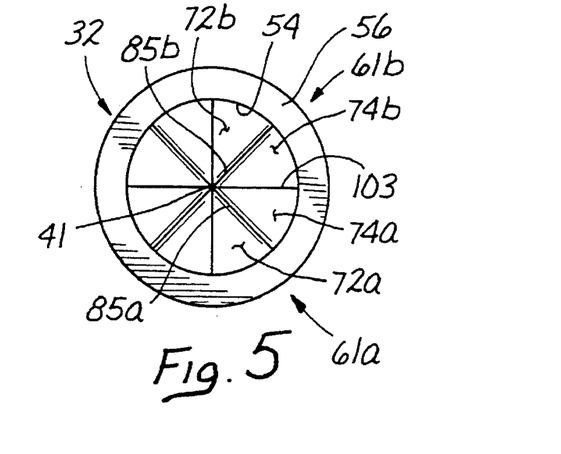
FIG. 5 is a rear elevation view taken along lines 5—5 of FIG. 3.

The folding section 61 includes a pair of walls 63 and 65 which have a respective outer surfaces 67, 70 and inner surfaces 72, 74 (best shown in FIG. 5). In a preferred embodiment the walls 63 and 65 are parallel and have a thickness such as 0.06 to 0.10 inches which is equivalent to the thickness of the outer wall 50.

Figure 2:
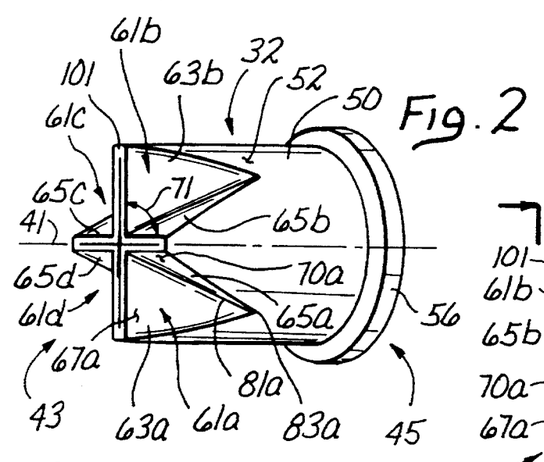
FIG. 2 is a perspective view of the zero closure valve illustrated in FIG. 1.
Figure 3:
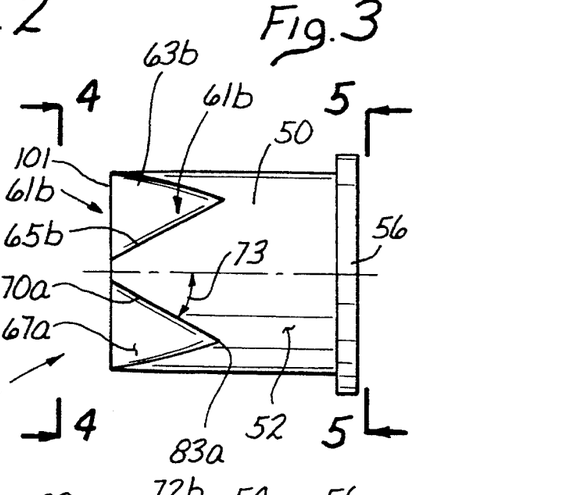
FIG. 3 is an enlarged side elevation view of the zero closure valve of FIG. 2.
Figure 4:
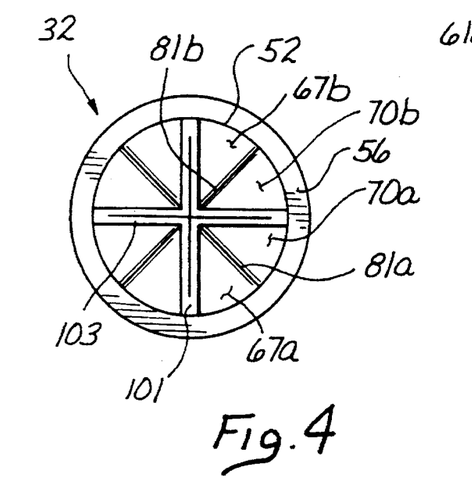
FIG. 4 is a front elevation view of the valve taken along lines 4—4 of FIG. 3.

The outer surfaces 67, 70, and inner surfaces 72, 74 are planar in this embodiment and extend at angles which are dependent in part on the number of folding sections 61. In the embodiment of FIG. 2, the walls 63, 65 associated with each folding section 61 intersect each other at a first angle, designated 71 in FIG. 2, and intersect the axis 41 at the a second angle, designated 73 in FIG. 3.

The first angle 71 between the associated walls 63, 65 will typically be equal to 360° divided by the number of folding sections 61. In the illustrated embodiment, this first angle 71 between the walls 63 and 65 is 90°. In an embodiment including only three of the folding sections 61, the first angle 71 typically would be 120°. In an embodiment including five of the folding sections 61 the first angle 71 typically would be 72°.

In a symmetrical embodiment, the second angle 73 between each of walls 63, 65 and the axis 41, would be equal. This angle, which in the preferred embodiment is 26°, could be increased to accommodate a shorter axial length for the valve 32, or decreased to accommodate a longer axial length for the valve 32.

In the illustrated embodiment, the surfaces 67a, 70a provide the folding section 61a with a generally concave outer surface and intersect each other along a line 81a. This line of intersection 81a extends radially outwardly with progressive proximal positions until it contacts the surface 52 at a point 83a. As point 83 moves progressively toward the flange 56 the second angle 73 between each of the surfaces 67a, 70a and the axis 41 is reduced. The distance between the point 83 and the flange 56 should be sufficient to allow adequate flexure of the material without enabling a set or otherwise overstressing the material. In a preferred embodiment, the valve 30 has an overall length of 1.125 inches and the flange 56 has an axial thickness of 0.125 inches. The distance between the point 83 and the flange is 0.50 inches; it follows that the point 83 in this embodiment lies approximately half the distance between the distal end of the valve 30 and the flange 56.

The friction forces created when the instrument 28 is moved within the valve 32 are associated with the configuration of the inner surfaces 72 and 74. With reference to FIG. 5, it will be noted that these surfaces 72, 74 in the fold section 61 have a generally convex configuration and intersect each other along a line 85 which extends radially inwardly with progressive distal positions. The same relationship of the surfaces 72, 74 and lines 85 can exist for each of the fold sections 61. Thus for the fold section 61b, the surfaces 72b and 74b have a convex configuration and meet to define an inner line 85b which extends radially inwardly with progressive distal positions along the valve 32.

Since the innermost extension of the surfaces 72 and 74 is the respective line 85, it follows that an instrument 28 introduced along the axis 41 contacts the valve 10 only along these lines 85a–d. The instrument 28 preferably makes no contact with the surfaces 72a–d and 74a–d. This result is highly advantageous since the area of contact between the valve 32 and the instrument 28 is greatly reduced. It follows that friction forces associated with the insertion and removal of the instrument 28 are also greatly reduced.

Figures 6, 7, 8:
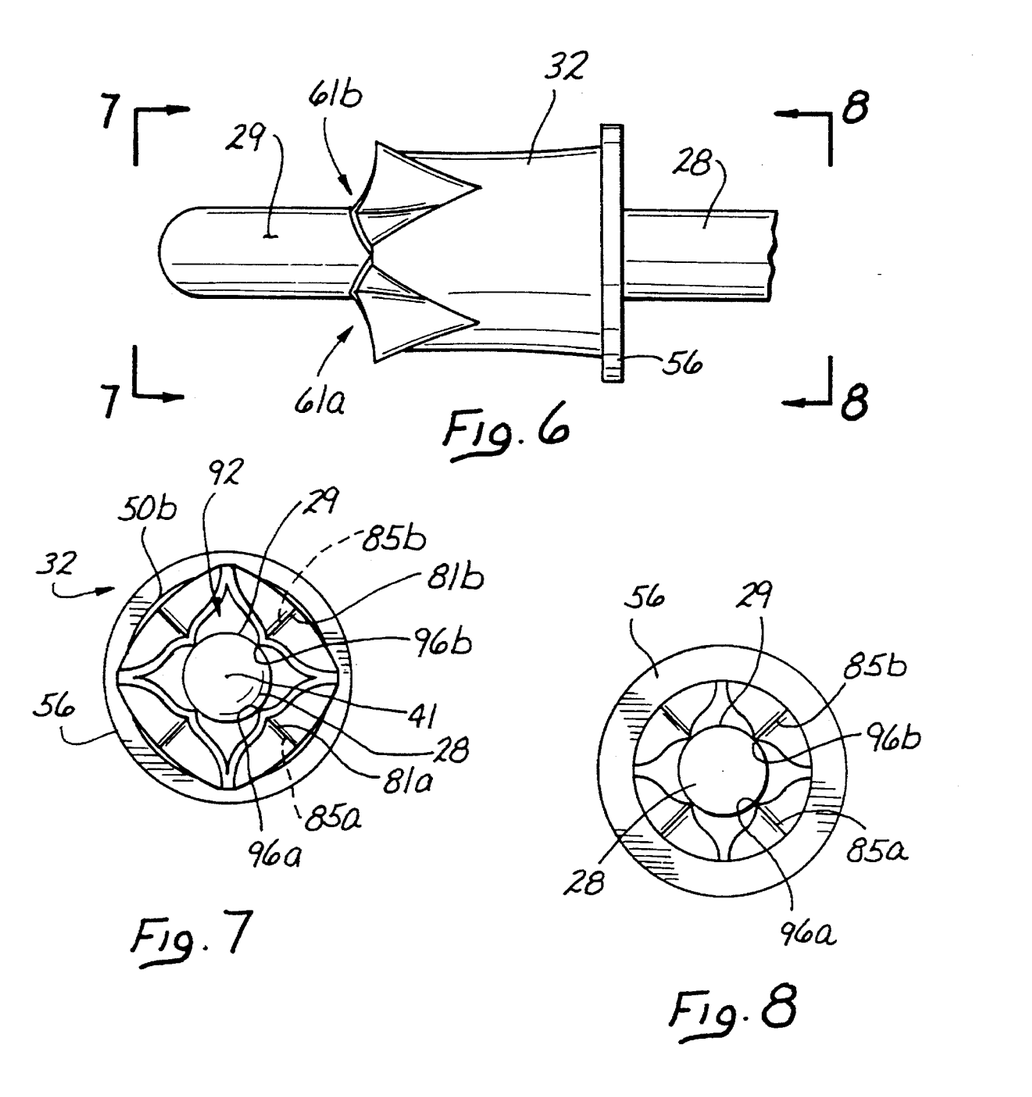
FIG. 6 is a side elevation view illustrating an instrument operatively positioned within the valve of FIG. 3.
FIG. 7 is a front elevation view taken along lines 7—7 of FIG. 6.
FIG. 8 is a rear elevation view taken along lines 8—8 of FIG. 6.

This feature relating to reduced friction is dramatically illustrated in FIGS. 6–8. As the instrument 28 is inserted into the valve 32 in its normally closed state, the fold sections 61 unfold to permit the instrument 28 to pass through the valve 32 in its open state. As the instrument 28 is inserted, its outer surface 29 contacts the valve 32 along the inner lines 85a–d forcing the fold section 61a–d radially outwardly to create and expand an opening 92 into the cannula 14. This opening 92 is best illustrated in the end views of FIG. 7 and FIG. 8. As the instrument 28 is introduced along the axis 41 it contacts the inner lines 85a–d along relatively short section designated 96a–d. Depending on the diameter of the instrument 28, this section 96a–d may be very short relative to the overall length of the line 85a–d, and in some cases, the section 96 of the line 85 may be substantially a point of contact. The narrower the line 85 and the shorter the section of contact 96, the lower the friction forces associated with insertion and removal of the instrument 28.

Although the seal 32 of the present invention is of particular interest for the low friction characteristics which it presents to the instrument 28, a primary purpose of the valve 32 is to provide a closure mechanism before the instrument 28 is inserted and after it is removed. In this case, the valve 32 provides a zero closure mechanism which is not possible with normal septum seals.

The zero closure state is best illustrated in FIG. 2 where it can be seen that the walls 63 and 65 which define the fold sections 61 extend distally to a surface 101 which is defined in a radial plane in this particular embodiment. As the instrument 28 is inserted into the valve 32, the valve moves from its normally closed state to an open state as illustrated in to FIGS. 6–8. The inner surfaces 72, 74 in adjacent fold sections 61 intersect along a slit 103 which extends from the inside of the seal 32 and through the distal surface 101. In a preferred embodiment each slit 103 extends from the inner surface 54 of the wall 50 to the axis 41. There is one slit for each of the fold sections 61. Thus in the illustrated embodiment including four of the fold section 61, there are four slits 103. If these four slits are equally spaced around the axis 41, alternate slits are co-planar and the slits 103 collectively define a cross.

Since a primary function of the valve 32 is to provide the zero closure mechanism it is important to consider the nature of the closure forces which exist in the absence of the instrument 28. The seal 32 is of particular advantage when it is disposed so that the surface 101 faces any fluid pressures such as those which may be associated with an insufflation gas, commonly used in laparoscopic surgery. Oriented in this direction, the outer surfaces 67, 70 associated with the walls 63 and 65, respectively, are oriented with at least a component facing distally of the valve 32. This presents the surfaces 67, 70 such that a fluid pressure on these surfaces will act to close the slits 103. In a particular embodiment wherein the surfaces 67, 70 are parallel to the slits 103, this component of force is directed perpendicular to the respective slit 103.

Figure 9:
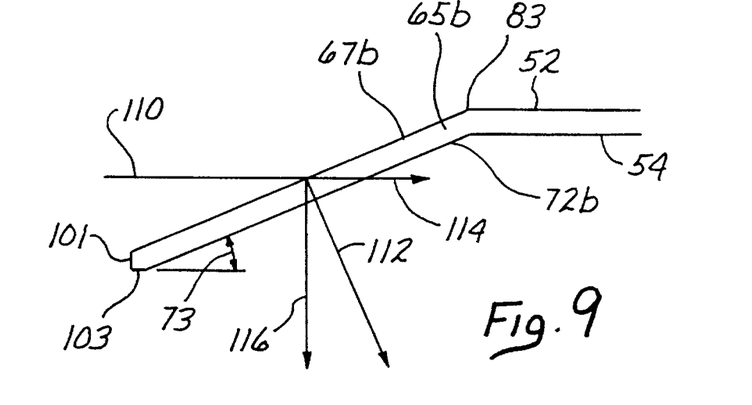
FIG. 9 is a diagram depicting closure forces typical for a valve of the present invention.

This can be better understood with reference to FIG. 9 wherein the wall 65b is shown in cross-section. In this diagram, an arrow 110 is representative of the axial direction from which fluid forces would emanate. As these forces impinge upon the outer surface 67b of the wall 65b, they create a force along arrow 112 which is perpendicular to the surface 67b. This arrow 112 can be separated into an axial component, represented by an arrow 114 and a radial component 116. It is the radial force represented by the arrow 116 which is perpendicular to the slit 103. Thus, response to the fluid pressure along the arrow 110 results in a component force along the arrow 116 which tends to move the slit 103 to a closed position.

It can now be seen that as the angle 73 between the surface 65b and the axis 41 increases, the length of the arrow 116 decreases providing a reduced closing force. This reduction in closing force must be compromised with the length of the valve 32 which can be reduced as the angle 73 increases. In the same manner, closing forces associated with the arrow 116 can be increased with a reduction in the angle 73 which will typically require a longer valve 32.

Figures 10, 11, 12:
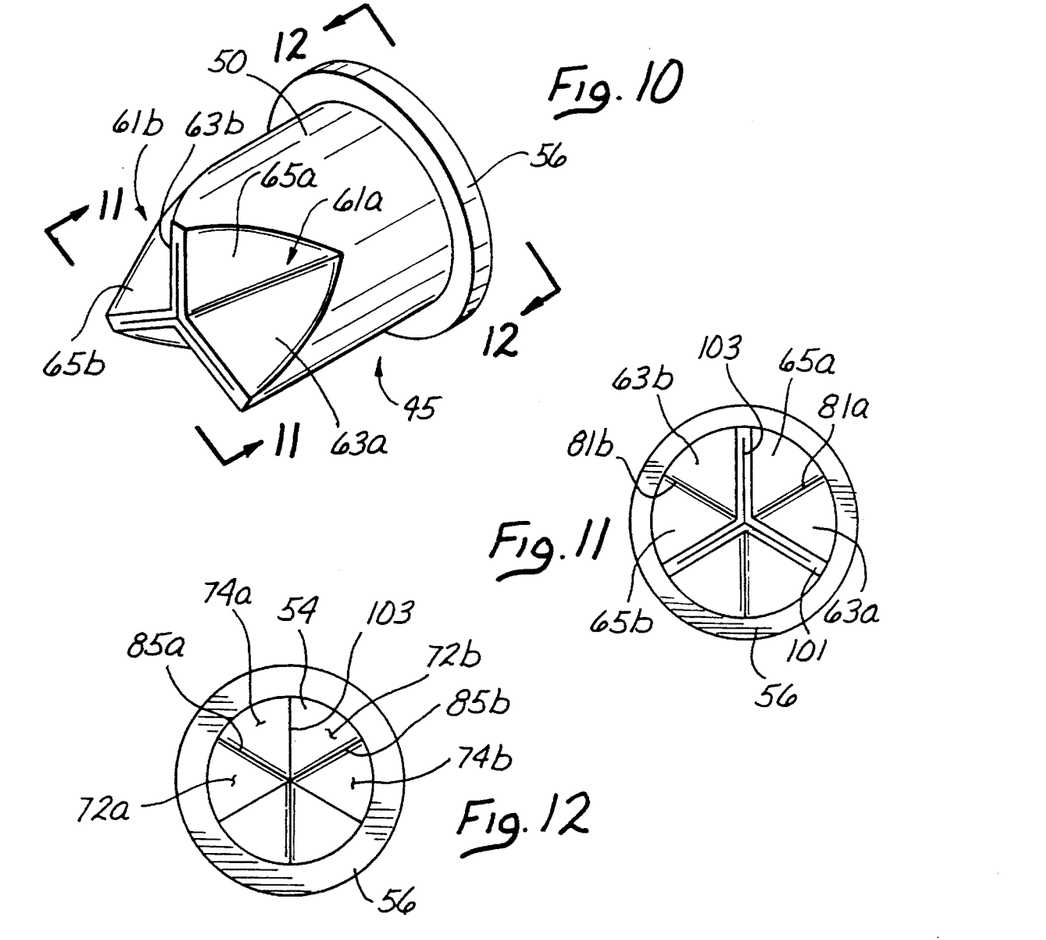
FIG. 10 is a perspective view similar to FIG. 2 of an embodiment including three fold sections.
FIG. 11 is a front elevation view taken along lines 11—11 of FIG. 10.
FIG. 12 is a rear elevation view taken along lines 12—12 of FIG. 10.

As previously mentioned, the concept of this invention is not to be limited by the number of folding sections 61. An embodiment of particular interest might include only three folding sections 61a–c as illustrated in FIGS. 10–12. In such an embodiment, the surfaces 67, 70 would be larger and for that reason could provide increased closing forces on the slits 103. Fewer folding sections 61 would also increase the circumferential distance separating the slits 103. This would equate to longer lever arms resisting the outward movement of the lines 81 as the valve 32 unfolds. Ultimately this could produce reduced friction forces opposing the entry of the instrument 28. With increased closing forces and decreased friction, this embodiment including three fold sections 61, could be of particular interest.

Also included in the invention is a preferred method for inserting the instrument 28 through the valve 32. In this method, the valve has the axis 41 and three or more of the fold sections 61. Each of these sections defines an opening such as the slit 103 and is movable between a first position wherein the slit 103 is in a closed state as illustrated in FIG. 2 and a second position wherein the slit 103 is in an open state as illustrated in FIG. 6. As the instrument 28 is introduced into the valve 32, it contacts the walls 63, 65 of the valve along the lines 85. With further insertion of the instrument, the fold sections 61 move from the closed first position to the open second position when the instrument 28 is ultimately removed from the valve 32, the fold sections 61 return from the open second state illustrated in FIG. 6 to the closed first state illustrated in FIG. 2.

Orienting the valve 32 so that the outer surfaces 70, 72 face in the distal direction makes the valve 32 particularly valuable for use in a pressurized environment. For example, when the cannula 14 is introduced into the abdominal cavity for laparoscopic surgery, a commonly used insufflation gas will exert a pressure on the distally facing outer surfaces 67, 70. As previously disclosed with reference to FIG. 9, the forces generated by the insufflation gas will tend to force the valve 32 to its zero closure state.

Figures 13, 18:
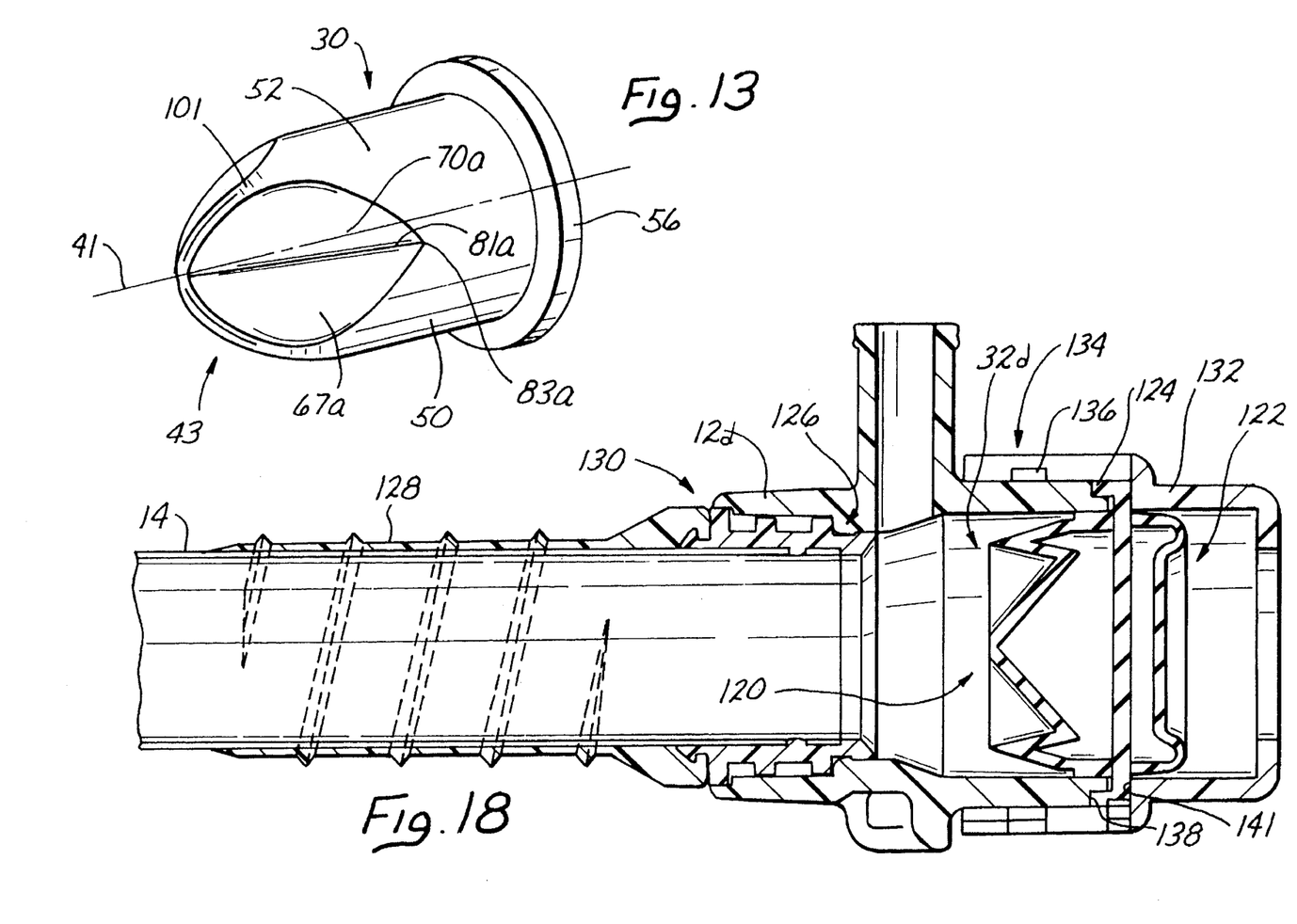
FIG. 13 is a perspective view of a further embodiment of the invention wherein the a distal end of the valve has a convex configuration.
FIG. 18 is an axial cross section of the trocar showing a compound valve in a further embodiment of the invention.

A further embodiment of the invention is illustrated in the perspective view of FIG. 13. This embodiment is similar to that illustrated in FIGS. 2 and 10 except that the distal end 43 of the valve 30 is generally curved. This curve is preferably convex so that the surface 101 at the distal end of the valve 30 extends decreasingly, radially, outwardly with progressive proximal positions along the axis 41. In a preferred embodiment, the surface 101, forms the quadrant of a circle. Thus the surface 101 is substantially perpendicular to the surface 52 at the axis 41 and substantially parallel to the axis 41 at the surface 52.

This particular embodiment having a curved distal end 43, has been found to offer improved characteristics for returning to its normal shape in the event of an inversion. While this feature is present to some extend in all of the foregoing embodiments, this particular embodiment appears to offer the greatest resistance to inversion and the greatest tendency for returning to its normal shape.

Figure 14:
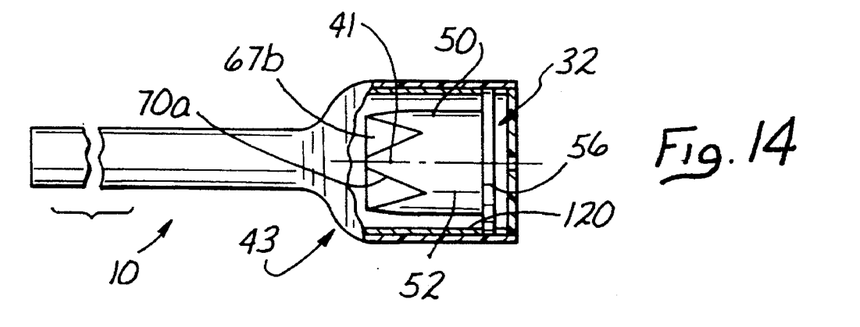
FIG. 14 is an axial cross section view of a further embodiment of the trocar and valve of the present invention.

A further embodiment of the invention is illustrated in FIG. 14 and includes a distal end 43 an outer wall 50 having an outer surface 52 and a proximal flange 56. In this embodiment, the distal end 43 can be configured similar to any of the embodiments previously discussed. It is the outer wall 50 which differs from the foregoing embodiments in that it has a frusto-conical configuration rather than a cylindrical configuration. Thus the wall 50 form a surface of rotation about axis 41 and extends radially inwardly with progressive distal positions along the axis 41.

This conical configuration of the outer wall 50 provides the valve 30 with significantly different characteristics which are of particular advantage when the instrument 28 is withdrawn. In the previous embodiments wherein the outer wall 50 has a generally cylindrical configuration, the valve 32 functions to prevent inversion when the instrument 28 is withdrawn. While a noninverting embodiment may be of advantage is some situations, in other cases, the inversion may be equally desirable. It has been found, for example, that inversion of the valve 32 in response to withdrawal of the instrument 28 functions to wipe the instrument 28 as it is withdrawn from the trocar 10.

Figure 15:
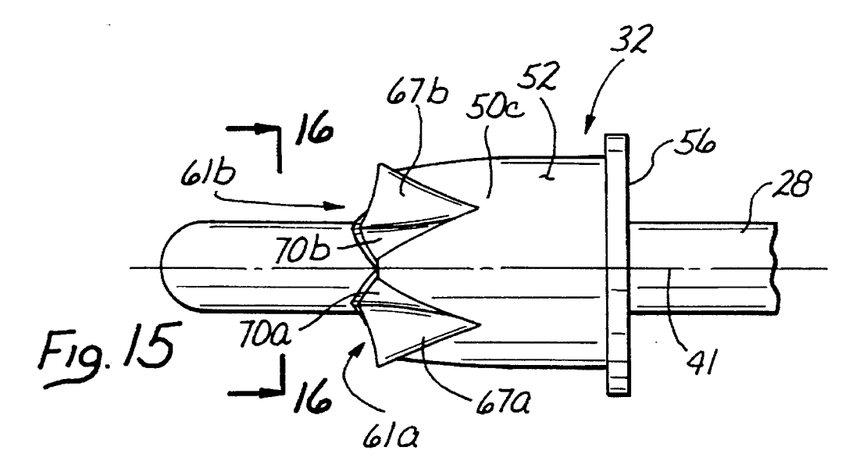
FIG. 15 is an axial cross section view of the valve illustrated in FIG. 14 with an instrument inserted into the valve.
Figure 16:
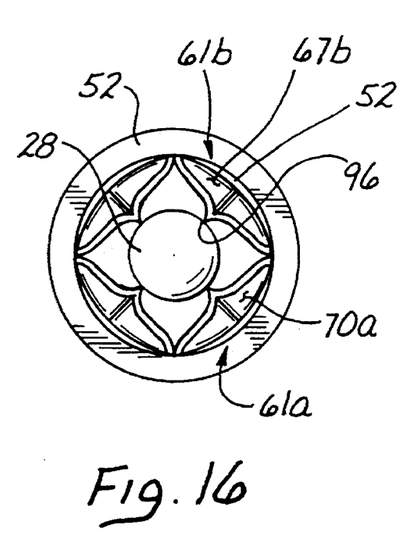
FIG. 16 is an end view and taken along lines 16—16 of FIG. 15.

This inversion of the outer wall 50 is facilitated in the embodiment of FIG. 14 by the conical configuration of the wall 50c. This can be more easily understood with reference to FIG. 15 which is similar to FIG. 6. An end view of this FIG. 15 is shown in FIG. 16. These figures best illustrate the forces present on the valve 32 as the instrument 28 is removed from the valve 32, into the page in FIG. 16. As the instrument 28 is withdrawn the frictional contact between the short section 96 of the valve 32 and the instrument 28, tends to curl the fold sections 61 inwardly. In the embodiment of FIG. 7, this curling is resisted by the cylindrical outer wall 50 which remains at a fixed radial distance from the axis 41 of the valve 32. In contrast the conical outer wall 50 in the embodiment of FIG. 16 diverges from the axis 41c in the proximal direction, so that any resistance to inversion is greatly reduced. As the instrument 28 is withdrawn the fold section 61 is encouraged to curl radially inwardly. Thus, the conical configuration of the outer wall 50c, which provides a circumference that increases with progressive proximal positions along the axis 41, actually facilitates inversion of the valve 32.

Figure 17:
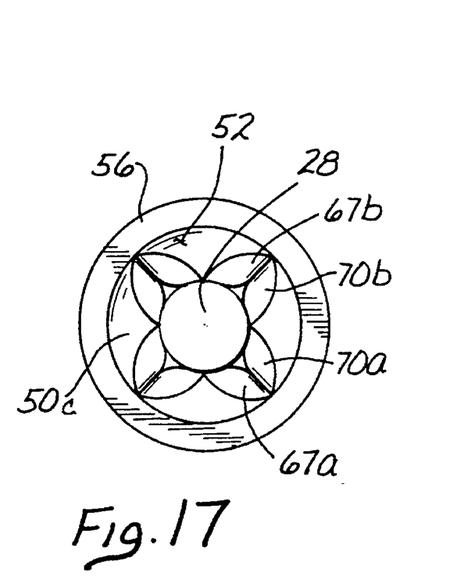
FIG. 17 is an end view similar to FIG. 16 and showing the instrument being withdrawn to promote inversion of the valve.

When the valve 32 inverts, the fold sections 61 turn outside in. The consequence of this inversion is to change contact with the instrument 28 from a line contact wherein the short sections 96 touch the instrument 28, to a surface contact wherein the outer surfaces of the fold sections 61, (for example the surfaces 67 and 70) touch the instrument 28. With this transition from line contact to surface contact, the entire outer surface of the instrument 28 can be wiped clean by the valve 32 as illustrated in FIG. 17.

In a further embodiment of the invention illustrated in FIG. 18, a valve 32 has a distal section 120 which can be similar to any of the embodiments previously discussed. This valve 32 also has an integral proximal section 122 in the form of a floating septum seal such as that disclosed and claimed in applicant's copending application Ser. No. 08/077,005 filed on Jun. 15, 1993 which is incorporated herein by reference. This combination valve 32d includes a circumferential ring 124 which is disposed between the distal section 120 and the proximal section 122. The trocar 10 of this embodiment includes the cannula 14d which is snap-fit to the housing 12d as shown by an arrow 126. A facial screw 128 is snap fit to the cannula 14d as shown by an arrow 130. A cap 132 is provided with a bayonet lock 134 which registers with tangs 136 carried by the housing 12d.

The housing 12d is provided with an annular recess 138 to receive the ring 124 of the valve 32d. With this ring sandwiched between the recess 138 of the housing 12d and a shoulder 141 on the cap 132, the outer surface of the valve 32d is effectively sealed around its perimeter to the housing 12d.

Although the invention has been disclosed with reference to specific embodiments and methods, it will be apparent to those skilled in the art that the concept can be structured in other embodiments, and the method can be carried out with other steps. For example, and without limitation, other embodiments might include more than four of the fold sections 61. Similarly, the outer surfaces 67, 70 defining the walls 64, 65 of the fold sections 61 could be angled in different directions. This angle of orientation may affect not only the closing forces but also the axial dimension of the valve 32 as previously discussed.

While the illustrated embodiments all terminate in a distal surface 101 which is disposed in a radial plane, it will be apparent that this distal surface can be disposed at other angles relative to the axis 41. Similarly, the symmetry illustrated and disclosed for the fold section 61, the surfaces 67 and 70, the length of the slits 103, and the length of the lines 81 and 85, could be varied to produce or asymmetrical embodiment.

The inner surfaces 54, 72 and 74 may also be varied in their respective shapes. Whenever possible, these various configurations should produce the point or line of contact, such as the line 85. As noted, this reduced area of contact will significantly reduce the friction forces associated with the insertion and removal of the instrument 28.

Figure 19:
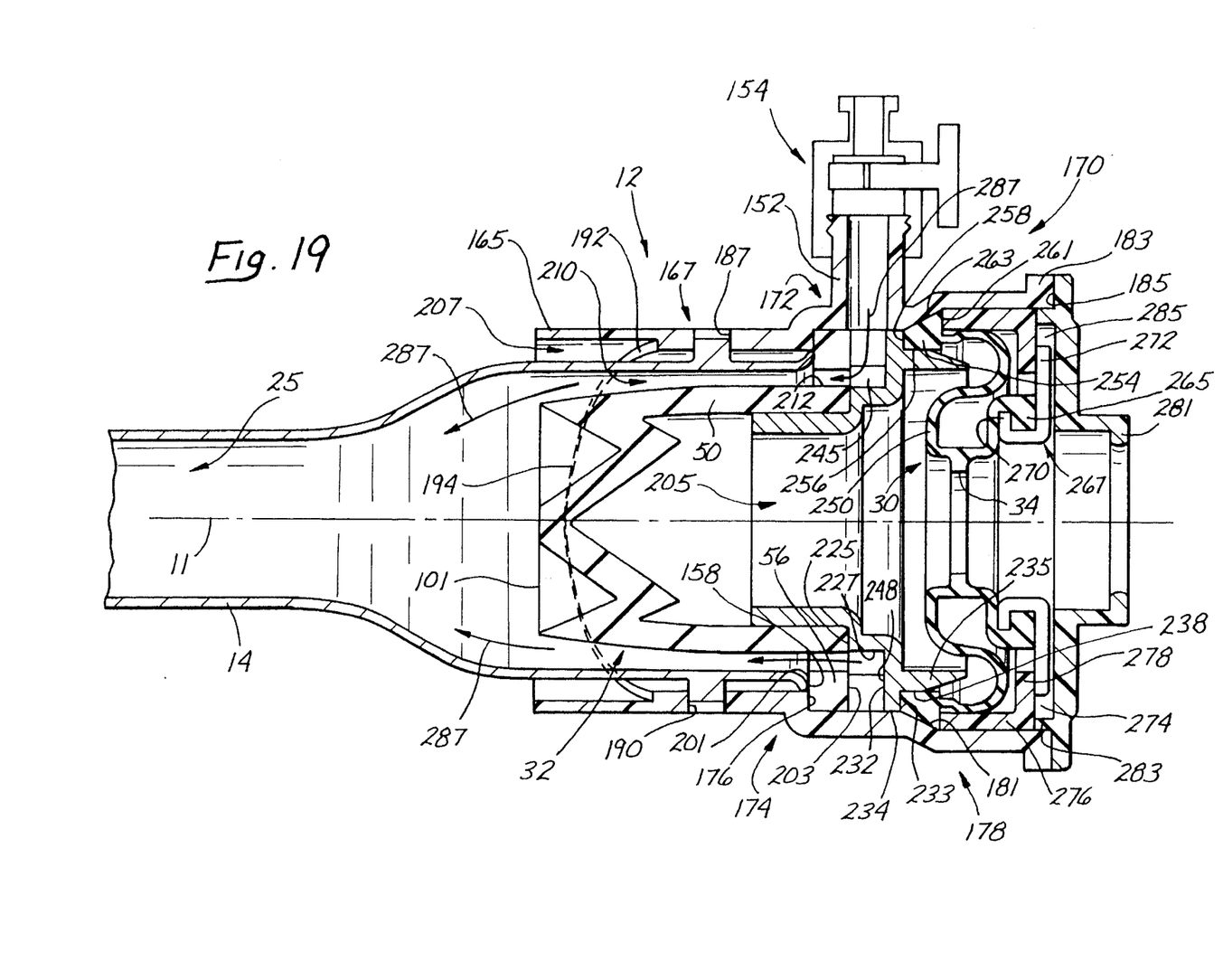
FIG. 19 is an axial cross sectional view of a trocar including a reusable cannula, a disposable seal housing, and an insufflation mechanism of the present invention.
Figure 20:
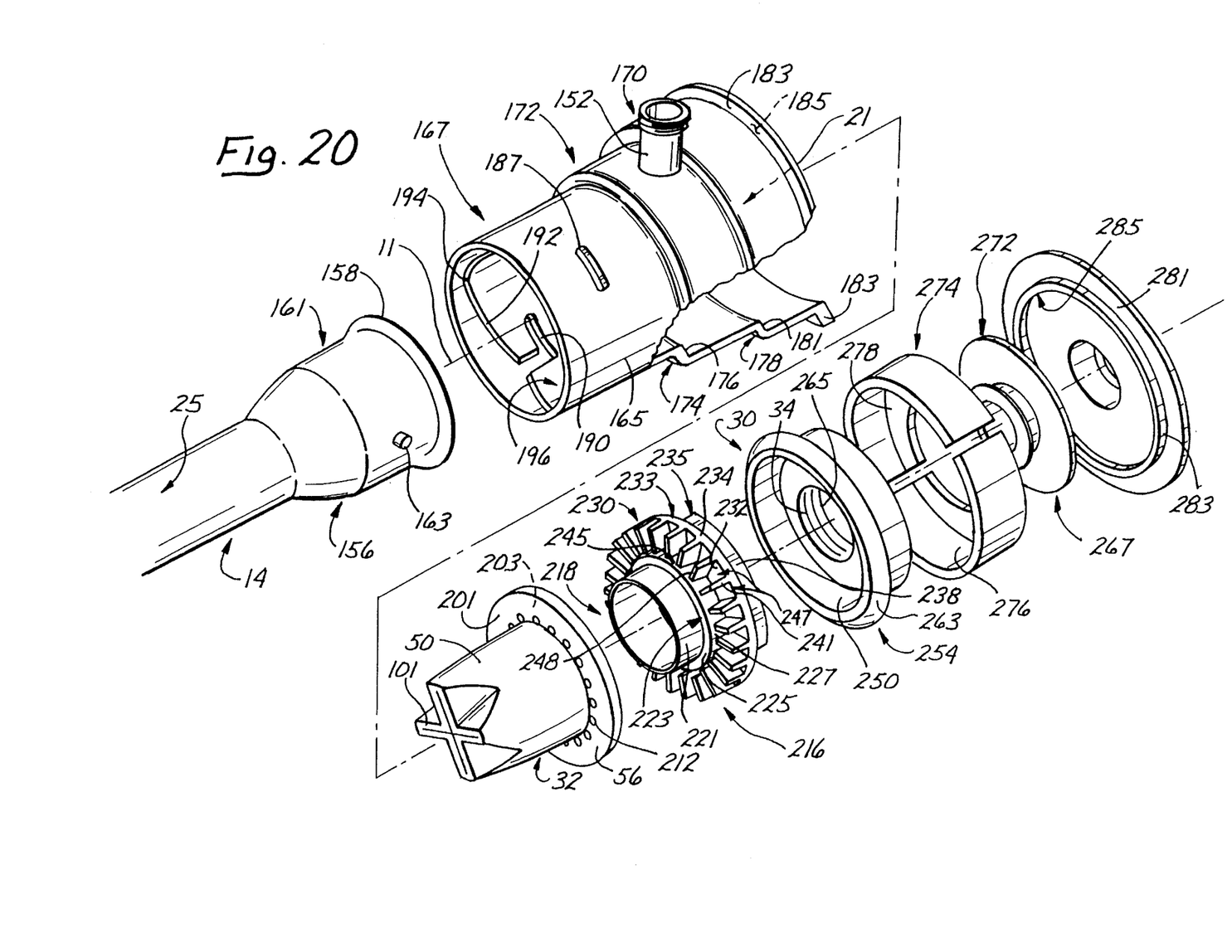
FIG. 20 is an expanded view of the trocar illustrated in FIG. 19, shown in perspective.

A further embodiment of the invention is illustrated in the assembled view of FIG. 19 and the expanded view of FIG. 20. This embodiment is of particular interest since it includes both reusable and disposable components. The reusable components, such as the cannula 14, can be formed from metal and can be sterilized for example in an autoclave. In this particular embodiment, there are not intricate structures associated with the cannula 14 so it is relatively easy to clean and sterilize for repeated use. By comparison, the housing 12 which supports the septum valve 30 and zero closure valve 32 is a relatively intricate structure which is best formed as a disposable subassembly.

An insufflation inlet 152 and insufflation valve 154, which in the past have commonly been provided as part of the cannula 14, are mounted on the disposable part of the trocar 10, more specifically the housing 12. The intricate structures associated with the inlet 152 and valve 154 would be difficult to clean if associated with the cannula 14. However, making these elements part of the disposable housing 12 avoids this complication.

The reusable cannula 14 is similar to those previously described in that it includes a lumen 25 which forms the working channel of the trocar 10. In the distal portions of the cannula 14, the lumen 25 is sized for insertion through the body wall 16. The proximal end of the cannula 14 includes an enlarged section 156 having a diameter which is sized and configured to register with the housing 12 in the manner described in greater detail below. At the proximal end of the cannula 14, this enlarged section 156 is flared radially outwardly to form a proximal facing surface 158. A pair of pins 161 and 163 extend radially outwardly at diametrically opposed positions on the enlarged portion 156.

The housing 12 in this embodiment has a wall 165 which is formed in three cylindrical portions 167, 170 and 172 which are concentrically disposed in end-to-end relationship along the housing 12. For example, the wall 165 includes a distal section 167, a proximal section 170, and a central section 172 disposed therebetween. Between the distal section 169 and central section 172, the wall 165 extends radially outwardly to form a shoulder 174 having a proximal facing surface 176.

A similar shoulder 178 is formed between the central section 172 and the proximal section 170. In this case, the shoulder 178 is inclined so that it extends outwardly as well as proximally along the housing 12. The shoulder 178 has an inner surface 181 which faces proximally and inwardly of the housing 12. At the proximal end of the proximal section 170, the wall 165 is provided with the flange 183 which extends radially outwardly with a surface 185 which faces in the proximal direction.

The distal section 167 of the housing 12 includes portions which define two slots 187 and 190. These slots 187, 190 are sized and configured to receive the pins 161 and 163, respectively, in order to form a bayonet connection between the cannula 14 and the housing 12. Accordingly, the slots 187 and 190 are diametrically opposed in this embodiment.

In the distal section 167 along the inner surface of the wall 165, a shoulder 192 forms an annular ramp which facilitates the bayonet connection between the pins 161, 163 and the associated slots 187, 190. The shoulder 192 starts at two distal points 194 and 196 which are diametrically opposed from each other and offset 90 degrees from the slots 187 and 190. From each of these distal points 194, 196, the shoulder 192 extends circumferentially and proximally toward each of the slots 187 and 190. Thus, in this embodiment, the shoulder 192 is formed with four quadrants, each extending from one of the distal points 194, 196 to one of the slots 187, 190. When the cannula 14 is assembled to the housing 12, the pins 161, 163 engage the shoulder 192 which ramps the pins 161, 163 towards the slots 187, 190 to facilitate the interlocking relationship of the housing 12 and cannula 14.

Also in the illustrated embodiment, it will be noted that the insufflation inlet 152 is preferably formed along the central section 172. Thus the inlet 152 provides fluid communication from regions exterior of the trocar 10, through the wall 165 in the central section 172, and into the inner chamber 121 of the housing 12.

The zero closure valve 32 can be embodied in any of the forms disclosed above. Each of these embodiments of the valve 32 includes the proximal flange 56 which extends radially outwardly from the outer wall 50 of the valve 32. This flange 56 provides the valve 32 with a distally facing surface 201 and a proximal facing surface 203. At the opposite end of the valve 32, the distal most surface is designate by the reference numeral 101.

When the valve 32 is initially loaded into the housing 12, typically in a housing subassembly, the flange 56 seats on the shoulder 174 with the surface 201 forming a seal with the surface 176. In this preferred disposition, the wall 50 of the valve 32 extends primarily along the distal section 167 of the housing 12.

In this position, the valve 32 divides the chamber 121 of the housing 12 into a region 205 proximal of the valve 32 and a region 207 distal of the valve 32. The proximal region 205 is defined as that portion of the chamber 121 having any portion of the valve 32 disposed distally or outwardly thereof. Conversely, the distal region 207 is defined as that portion of the chamber 121 having any portion of the valve 32 disposed inwardly or proximally thereof. Specifically included in the proximal region 205 is that portion of the chamber 21 which is disposed proximally of the flange 56. Specifically included in the distal region 207 is an annular passage 210 which extends between the wall 50 of the valve 32 and the wall 165 of the housing 12. A plurality of holes 212 extend axially through the flange 56 to provide fluid communication between the regions 205 proximal of the valve 32 and the passage 210 of the regions 207 distal of the valve 32.

A manifold 216 is best illustrated in the perspective view of FIG. 19. In this embodiment, the manifold 216 is formed as four integral cylinders extending in a concentric end-to-end relationship along the axis 11 of the trocar 10. A first cylinder 218 has an outer cylindrical surface 221 with a first diameter. A second cylinder 223, disposed proximally of the first cylinder 218, has an annular surface 225 facing distally, and an outer cylindrical surface 227 with a second diameter greater than the first diameter. A third cylinder 230, disposed proximally of the second cylinder 223, is defined by an annular surface 232 which faces distally, an annular surface 233 which faces proximally, and an outer cylindrical surface 234 with a third diameter greater than the second diameter. A fourth cylinder 235, disposed proximally of the third cylinder 230, is defined by an outer cylindrical surface 238 with a fourth diameter less than the third diameter but greater then the second diameter.

A plurality of walls 241 extend radially and distally in a cantilevered relationship with the third cylinder 230. These walls 241 extend along the surface 232 radially inwardly from the surface 234. However, they are stopped short of the surface 227 associated with the second cylinder 223, so that an annular manifold chamber 245 is formed outwardly of the second cylinder 223 but inwardly of the walls 241. Each of the walls 241 extends from the surface 232 distally to a surface 248 which is disposed in the same radial plane as the surface 225 in the illustrated embodiment. These walls 241 form a fenestration of windows 247 each of which extends radially outwardly from the manifold chamber 245 to the outer surface 234.

During manufacture of the housing subassembly, the manifold 216 is loaded into the housing 12 after the valve 32. It is moved distally in the proximal region 205 of the chamber 21 until the surface 225 of the second cylinder 223 engages the proximal facing surface 203 of the wall 50. At this point, each of the surfaces 248 associated with the walls 241 will contact the surface 203 of the flange 56. The surface 234 associated with the third cylinder 230, will be disposed in close proximity to the wall 165 of the housing 12.

In the illustrated embodiment, the insufflation inlet 152 is positioned on the central cylinder 172 of the housing 12 in fluid communication with the fenestration of windows 247 of the manifold 216.

In a preferred embodiment, the septum seal 30 is formed as a floating valve such as that disclosed and claimed in applicant's copending application Ser. No. 08/077,005. The septum valve 30 includes an annular wall 250, portions of which define the aperture 34 which is sized and configured to receive the instrument 28, as illustrated in FIG. 1. Distally of the aperture 34, the wall 250 has a bellows configuration which permits the aperture 34 to move laterally in order to accommodate an instrument 28 inserted off axis. At the distal end of the wall 250, a sealing ring 254 is formed with an inwardly facing surface 256, a distally facing surface 258, a proximal facing surface 261 and a surface 263 which faces outwardly and distally. Thus, in cross-section, the sealing ring 254 has a trapezoidal configuration.

At the end of the wall 250 proximally of the aperture 234, an annular lip 265 is formed to receive an annular ring 267 which floats with the aperture 34. In cross-section, this ring 267 has the configuration of the letter "J" with a short leg 270 and a long leg 272. The short leg 270 forms an annulus which is captured by the lip 265 while the long leg 272 forms an annulus which extends along a radius of the axis 11.

When the valve 30 is operatively positioned within the housing 12, the surfaces 256 and 258 of the sealing ring 254 are brought into contact with the respective surfaces 238 and 233 of the manifold 216. The surface 263 is also brought into contact with the inner surface 181 of the shoulder 178.

A sealing enhancement ring 274 is formed as a toroid having the cross-section of the letter "L". This cross-section includes a long leg 276 and a short leg 278. In a preferred embodiment, the ring 274 is formed in two semi-circular portions which are inserted with the valve 30 and the float ring 267 into the housing 12. In this position, the long leg 276 of the seal enhancement ring 274 forms an annulus which is positioned in juxtaposition to the wall 165 of the housing 12. The distal end of the annulus formed by the leg 276 is brought to bear against the surface 261 of the sealing ring 254 and presses axially distally against that surface.

This pressure is enhanced by the force fit of a cap 281 which can be sonic welded to the surface 185 of the flange 183 at the proximal end of the housing 12. This cap 281 includes an annular tang 283 which presses axially on the annulus formed by the long leg 276. This increases the pressure on the surface 261 to maintain seals between the contacting surfaces 176 and 201, 203 and 225, 203 and 248, 233 and 258, 181 and 263, and 238 and 256.

A feature of importance to operation of the floating seal 30 is the formation of an annular chamber 285 between the cap 281 and the annulus formed by the short leg 278 of the ring 274. This annular chamber 285 has a diameter which is greater than the outside diameter of the annulus formed by the long leg 272 of the float ring 267. Accordingly, the ring 267 and the aperture 34 of the valve 30 are free to float radially within the chamber 285.

The housing subassembly including the housing 12, valve 32, manifold 216, valve 30, rings 267 and 274 is completed with attachment of the cap 281. With the resulting configuration, best illustrated in FIG. 19, it will be noted that the insufflation inlet 252 forms a passage illustrated by arrows 287, which extends in fluid communication through the wall 165, into the regions 205 proximal of the valve 32, and into the regions 207 distal of the valve 32. More specifically, in the illustrated embodiment this passage 287 extends from the inlet 152, through the wall 165, and into the windows 247 which are in communication with the inlet 152. From the windows 247 the passage 287 extends into the annular manifold chamber 245 and through the holes 212 in the flange 183 of the valve 32. On the distal side of the holes 212, the passage 287 extends into the passage 210 outwardly of the valve 32 and inwardly of the cannula 14.

As a disposable component, the housing subassembly will typically be provided to a user who is already in possession of the cannula 14. This reusable sterilizable cannula 14 can be inserted into the distal end of the housing 12 where the pins 161 will engage the shoulder 192 of the ramp which guides the pins 161, 163 into engagement with the associated slots 187 and 190. In this location, the flare at the proximal end of the cannula 14 will place the surface 158 in sealing engagement with the distally facing surface 201 of the valve 32.

In operation, the trocar 10 will be inserted through the body wall 16 until the distal end of the cannula 14 is positioned within the insufflated body cavity 18. In this position, the back pressure of the insufflation gas will close the zero closure valve 32 so that insufflation is maintained. When the instrument 28 is inserted into the trocar 10, the zero closure valve 32 will open but the aperture 34 of the valve 30 will form a seal around the outer surface 29 of the instrument 28. Whether the instrument 28 is present within or absent from the trocar 10, insufflation can be controlled by operation of the valve 154 associated with the inlet 152. With the cannula 14 in place, the insufflation fluid will pass through the holes 212 and into that portion of the passage 210 which is disposed within the lumen 25 of the cannula 14.

It is of interest in the illustrated embodiment that the flange 183 of the valve 32 is positioned to form a seal not only with the cannula 14, but also with the manifold 216. No additional "O" rings or other elastomeric material is relied on for this purpose. The holes 212 through the flange 183 enable the inlet 152 to be positioned along the housing 12 so that it is in fluid communication with the regions 205 proximal of the valve 32. With the manifold 216 configured with the fenestration of windows 247, insufflation can occur in this region 205, through the manifold by having the reusable cannula 14 separated from the intricate disposable components associated with the housing 12.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A trocar having a working channel extending along an axis between a distal end and proximal end, the trocar comprising:

a cannula having a tubular configuration and a wall which defines the working channel at the distal end of the trocar;

a housing disposed in fixed relationship to the cannula and defining the working channel at the proximal end of the trocar;

a valve disposed in the working channel and separating the channel into regions proximal of the valve and regions distal of the valve;

elastomeric means included in the valve and forming a first seal which is openably closable across the working channel;

a wall included in the valve and extending radially outwardly of the elastomeric means;

portions of the housing engaging the valve wall and forming with the valve wall a second seal which is disposed generally outwardly of the first seal;

means for defining a passage extending from regions exterior of the trocar, through the regions proximal of the valve, and into the regions distal of the valve;

a housing inlet included in the passage defining means, the housing inlet defining a first section of the passage which extends through the housing to provide fluid communication between the regions exterior of the trocar and the regions proximal of the valve;

valve means disposed across the housing inlet for openably closing the first section of the passage to thereby control the administration of a fluid from the regions exterior of the trocar, through the passage and into the working channel of the cannula;

portions of the valve being included in the passage defining means and defining a second section of the passage between the first seal and the second seal; and a manifold included in the passage defining means and defining a third section of the passage between the first section of the passage and the second section of the passage.

2. The trocar recited in claim 1 wherein the valve wall includes an annular flange extending transverse to the working channel and the portions of the valve define the second section of the passage in the form of at least one hole extending through the annular flange.

3. The trocar recite in claim 2 wherein the manifold includes:

a multiplicity of walls defining a fenestration of windows, at least one of the windows being disposed in fluid communication with the inlet of the housing and the at least one hole in the annular flange of the valve.

4. The trocar recited in claim 3 wherein the annular flange is sandwiched between the portions of the housing and the walls of the manifold to create the second seal between the valve and the housing.

5. The trocar recited in claim 1 wherein the valve is a double duck bill valve.

6. The trocar recited in claim 3 wherein the manifold further comprises:

means defining a distribution chamber in fluid communication with each of the windows in the fenestration of windows and in fluid communication with each of the holes in the annular flange.

7. A trocar having a working channel extending along an axis between a proximal end and a distal end, comprising:

a cannula having a first axis and a tubular configuration with a wall which extends distally from a proximal end of the cannula to define the working channel at the distal end of the trocar;

a housing having a second axis and a wall which extends proximally from a distal end of the housing to at least partially define the working channel at the proximal end of the trocar;

at least one seal disposed in the housing across the working channel and proximally of the distal end of the housing;

one of the cannula and the seal housing being formed of a sterilizable metal material so that it may be reusable in a plurality of medical procedures;

the other of the cannula and the seal housing being formed of a disposable plastic material; and means disposed at the proximal end of the cannula and the distal end of the housing for releasably joining the cannula to the housing with the first axis aligned with the second axis to define the working channel of the trocar, said joining means being adapted to permit easy attachment and detachment of the cannula and the housing.

8. The trocar recited in claim 7 wherein the joining means includes a bayonet connector comprising:

at least one tab disposed at one of the proximal end of the cannula and the distal end of the housing;

means defining at least one recess at the other of the proximal end of the cannula and the distal end of the housing, the at least one recess being sized and configured to receive the at least one tab and to removably fix the cannula to the housing; and means disposed at the other of the proximal end of the cannula and the distal end of the housing for slidingly engaging the at least one tab and for guiding the at least one tab toward the means defining at least one recess.

9. The trocar recited in claim 8 wherein the at least one tab is disposed at the proximal end of the cannula and the means for defining the at least one recess is disposed at the distal end of the housing.

10. The trocar recited in claim 9 wherein the engaging means comprises a ramp extending from a distal position on the housing radially proximally to the means defining the at least one recess, the ramp being configured to receive the at least one tab and to slidingly engage the at least one tab and to guide the at least one tab toward the means defining the at least one recess.

11. The trocar recited in claim 8 wherein the at least one tab includes at least two tabs diametrically opposed at the one of the distal end of the housing and the proximal end of the cannula.

12. The trocar recited in claim 9 wherein the at least one tab extends radially outwardly of the wall of the cannula.

13. The trocar recited in claim 7, wherein the cannula is formed of a sterilizable metal material and the seal housing is formed of a disposable plastic material.

14. The trocar recited in claim 13, wherein the entire seal housing, including the components enclosed thereby, is adapted to be detached from the cannula and disposed of after a single use.

* * * * *